US005638637A

United States Patent [19]
Wong et al.

[11] Patent Number: 5,638,637
[45] Date of Patent: Jun. 17, 1997

[54] PRODUCTION OF IMPROVED RAPESEED EXHIBITING AN ENHANCED OLEIC ACID CONTENT

[75] Inventors: Raymond S. C. Wong; Wallace D. Beversdorf; James R. Castagno; Ian Grant; Jayantilal D. Patel, all of Ontario, Canada

[73] Assignee: Pioneer Hi-Bred International, Inc., Des Moines, Iowa

[21] Appl. No.: 286,708

[22] Filed: Dec. 20, 1988

Related U.S. Application Data

[63] Continuation-in-part of Ser. No. 140,139, Dec. 31, 1987, abandoned.

[51] Int. Cl.$^6$ ............................ A01H 1/04; A01H 1/06; A01H 5/10
[52] U.S. Cl. ..................... 47/58; 47/DIG. 1; 800/200; 800/230; 800/DIG. 17; 800/DIG. 69
[58] Field of Search ........................ 47/58, DIG. 1; 435/212, 134, 240.5; 800/1, 200, 205, DIG. 15, DIG. 16, DIG. 17, DIG. 69; 426/601, 611; 514/552, 557, 558, 560

[56] References Cited

U.S. PATENT DOCUMENTS

| | | | |
|---|---|---|---|
| 4,277,412 | 7/1981 | Logan | 554/193 |
| 4,297,292 | 10/1981 | Logan et al. | 554/187 |
| 4,517,763 | 5/1985 | Beversdorf et al. | 47/58 |
| 4,627,192 | 12/1986 | Fick | 47/58 |
| 4,658,084 | 4/1987 | Beversdorf et al. | 800/1 |
| 4,658,085 | 4/1987 | Beversdorf et al. | 800/1 |
| 4,743,402 | 5/1988 | Fick . | |
| 4,948,811 | 8/1990 | Spinner et al. | 514/560 |

FOREIGN PATENT DOCUMENTS

| | | | |
|---|---|---|---|
| 0255377 | 3/1988 | European Pat. Off. | 435/240.5 |
| 0255378 | 3/1988 | European Pat. Off. | 435/240.5 |
| 1814440 | 7/1969 | Germany . | |
| 0237997 | 11/1985 | Japan | 435/134 |
| 1212118 | 11/1970 | United Kingdom | 47/58 |
| WO92/03919 | 3/1992 | WIPO . | |

OTHER PUBLICATIONS

Dawn, J.K., et al (1982) "Use of Gas Liquid Chromatography for Monitoring the Fatty Acid Composition of Canadian Rapeseed" J.A.O.C.S., vol. 60, No. 10, pp. 1751–1754.

Stefansson, B.R. "The Development of Improved Rapeseed Cultivars (Chapter 6)" *High and Low Erucic Acid Rapeseed Oils* Academic Press, Inc. Canada 1983 (pp. 143–159).

Pleines, S. et al. (1988) "Breeding for Improved C18–Fatty Acid Composition in Rapeseed (*Brassica napus* L.)" *Fat Sci. Technol.* vol. 90, No. 5 pp. 167–171.

Diepenbrock, W., et al. (1987) "Genetic Regulation of Linolenic Acid Concentration in Rapeseed" *Crop Sci.* vol. 27 pp. 75–77.

Kondra, Z.P., et al (1976) "Selection for Oleic, Linoleic and Linolenic Acid Content in F2 Populations of Rape" *Can. J. Plant Sci.* vol. 56 pp. 961–966.

Brunklaus–Jung, E., et al. (1987) "Genetical and Physiological Investigations on Mutants for Polyenoic Fatty Acids in Rapeseeds (*Brassica napus*, L.) III Breeding Behaviour and Performance" *Plant Breeding* vol. 98 pp. 9–16.

Brunklaus–Jung, E., (1986) "Genetical and Physiological Investigations on Mutants for Polyenoic Fatty Acids in Rapeseed (*Brassica napus*, L.) IV Fatty Acid Composition on Leaf Lipids and Luminescence" *Angew Botanik* vol. 60 pp. 333–338.

Wahhab, M.A., et al (1980) "Selection of Mustard Plants (*Brassica juncea* L.) with Low Content of Linolenic Acid" *Bangladesh J. Agril. Sci* vol. 7 No. 2, pp. 105–111.

Diepenbrock, W. (1984) "The Fatty Acid Composition of Glactolipids and Triglyceride from Rapeseed Plants (*Brassica napus* L.) as Affected by Genotype" *Angew. Botanik* vol. 58, pp. 371–379.

Srivastava, V.K., et al (1976) "Comparison of Some Chemical Characteristics of Indian and Canadian Brassica Seeds" *The Ind. J. Nutr. Dietet.*, vol. 13, pp. 336–342.

Evans, D.E., et al (1988) "Correlations Between Gametophytic (Pollen) and Sporophytic (Seed) Generations for Polyunsaturated Fatty Acids in Oilseed Rape *Brassica napus* L." *Theor. Appl. Genet.* vol. 76 pp. 411–419.

Beach, D.H.C., "Chapter 8: Rapeseed Crushing and Extraction" from *High and Low Erucic Acid Rapeseed Oils* Academic Press, Canada 1983 (pp. 181–195).

Rahman, L. (1978) "Relationships Between Major Fatty Acids of Oleiferous Species of Brassica" *Indian J. Agric. Sci.* vol. 48(7) pp. 401–406.

King, P.J. "Chapter 61: Mutagenesis of Cultured Cells" *Cell Culture and Somatic Cell Genetics of Plants* vol. 1, Vasil, I.K. (Ed.) Academic Press, Inc., Orlando 1984, pp. 547–549.

Roy, N.N., et al. (1985) "TXLIN—An Interspecific Source for High Linoleic and Low Linolenic Acid Content in Rapeseed *Brassica napus* L" *Z Pflanzenzuchtg.* vol. 95 pp. 201–209.

(List continued on next page.)

Primary Examiner—James R. Feyrer
Attorney, Agent, or Firm—Burns, Doane, Swecker & Mathis, L.L.P.

[57] ABSTRACT

Improved rape plants, seeds capable of forming the same, and a novel improved endogenous vegetable oil derived from the rapeseeds are provided. Such plants have the ability to yield an endogenous vegetable oil of increased heat stability in combination with other desirable traits. The increased stability of the vegetable oil is attributable to the presence of an unusually high oleic acid content in the rapeseeds which has been lacking in the available rape plants of the prior art. It has been found that the novel rape plants of the present invention reliably can be formed by mutagenesis followed by selection as described. The vegetable oil produced by the improved rape plants of the present invention is particularly well suited for use as a frying oil wherein the increased stability at elevated temperatures is of prime importance. In a preferred embodiment wherein the vegetable oil is used as a frying oil, the alpha-linolenic acid content concomitantly is reduced which additionally imparts an increased oxidative stability.

59 Claims, No Drawings

OTHER PUBLICATIONS

Roy, N.N., et al. (1986) "Development of Near–Zero Linolenic Acid (18:3) Lines of Rapeseed (*Brassica napus* L.)" *Z Pflanzenzuchtg* vol. 96 pp. 218–223.

Rakow, G., et al. (1975) "Oil, Fatty Acid and Chlorophyll Accumulation in Developing Seeds of Two Linolenic Acid Lines of Low Eurcic Acid Rapeseed" *Canadian J. Plant Science* vol. 55 pp. 197–203.

Mattson, F.H., et al. (1985) "Comparison of Effects of Dietary Saturated, Monosaturated, and Polyunsaturated Fatty Acids on Plasma Lipids and Lipoproteins in Man" *Journal of Lipid Research* vol. 26, 1985 pp. 194–202.

Downey, R.K., et al. (1963) "Methods of Breeding for Oil Quality in Rape" *Canadian Journal of Plant Science* vol. 43 pp. 271–275.

Downey, R.K., et al. (1971) "Genetic Control of Fatty Acid Composition in Oilseed Crops" Proc. Flax. Inst. U.S.A. vol. 41 No. 3 pp. 1–3.

Rakow, G. et al. (1973) "Opportunities and Problems in Modification of Levels of Rapeseed $C_{18}$ Unsaturated Fatty Acids" *J. Am. Oil Chem. Soc.* 50(10) pp. 400–403.

Roy, N.N., et al. (1987) "Prospects for the Development of Rapeseed (*B. napus*) with Improved Linoleic and Linolenic Acid Content" *Plant Breeding* vol. 98 pp. 89–96.

Pleines, S., et al. (1987) "Recurrent Selection for Modified Polyenoic Fatty Acid Composition in Rapeseed (*Brassica napus* L.)" *7th International Rapeseed Congress* GC/RC p. 23.

Robbelan, G. et al. (1975) "Genetical and Physiological Investigations on Mutants for Polyenoic Fatty Acids in Rapeseed, *Brassica napus* L." *Z. Pflanzenzucht* vol. 75 pp. 93–105.

Rakow, G. (1973) "Selektion auf Lino–und Linolensaueregehalt in Rapssamen nach mutagener Belrandlung" *Z. Pflanzenzucht* vol. 69 pp. 62–82 (English Translation).

Robbelen, G. "Changes and Limitations of Breeding for Improved Polyenoic Fatty Acids Content in Rapeseed (Chapter 10)" *Biotechnology for the Oils and Fats Industry* Ratledge, C., et al. (Eds.) Amer. Oil Chemists Society Monogram 11 pp. 97–105 dated 1984.

Töpfer, R., et al., (1995) "Modification of Plant Lipid Synthesis" *Science* vol. 268, pp. 681–686.

"Genetic Control of Linolenic Acid Concentration in Seed Oil of Rapeseed (*Brassica napus* L.)", *Theor. Appl. Genet.*, vol. 78, pp. 793–797 (1989), by S. Pleines and W. Friedt.

"Canola Filing", *Bio Engineering News*, vol. 11, No. 34, p. 1 (Aug. 10, 1990).

"Untersuchungen über die genotypische Variation des C18–Fettsäuremusters bei Raps (*Brassica napus* L.) und Möglichkeiten ihrer züchterischen Nutzung". Inaugural Dissertation of Stephan Pleines to obtain the degree of Dr. in the field of agricultural sciences at the Justus–Liebig University Giessen.

English translation of above entitled, "Investigation of the Genotypical Variation of the C18–Fatty Acid in Rape (*Brassica napus* L.) and Possible Application to Breeding".

"Breeding Rapeseed for Oil and Meal Quality" by R.K. Downey, B.M. Craig, and C.G. Youngs, Journal of the American Oil Chemists' Society, vol. 46, pp. 121 to 123 (Mar. 1969).

"Rapeseed" by Appelquist and Ohlson, published by Elsivier (1972). pp. 117 to 122.

"Rape and Mustard Breeding for Oil Quality" by V.I. Shopta of the U.S.S.R. Proceedings International Rapeseed Conference, Pornan, Poland (May 1987). pp. 560 to 565.

"Breeding of Improved Oil and Meal Quality in Rape (*Brassica napus* L.) and turnip rape (*Brassica campestris* L.)", Roland Jönsson, *Hereditas*, 87:205 to 218 (1977).

Kvalitetsförädling av oljeväxter–resultat och möjligheter, Roland Jönsson, *Sveriges Utsadosforenings Tidskrift*, 94, pp. 36 to 38 (1984). (An English Translation also is provided.).

"Genotypes for High Oleic Acid Content (About 80%) in the Oil of Rapeseed (*Brassica napus* L.)", B.Y. Chen and B. Gertsson, *Crucif. Newsletter*, 13, pp. 46 and 47 (1988).

Nutzpflanzen der Tropen und Subtropen, vol. IV, Pflanzenzüchtung, Armin Fuchs, S. Hirzel Verlag, Leipzig, pp. 155 to 177 (1980). (An English translation also is provided.).

Project Plan and Application for Contribution of Svalöf AB of Svalöv, Sweden, dated Feb. 25, 1986, by Dr. Roland Jonsson. (An English translation also is provided.).

Project Plan and Application for Contribution of Svalöf AB of Svalöv, Sweden, dated Feb. 23, 1987 by Dr. Roland Jonsson. (An English translation also is provided.).

Abstract of Lecture Delivered by S. Pleines and W. Friedt at 43rd Lecture Meeting of Deutsche Gesellschaft für Fettwissenschaft in Hamburg, Sep. 30 and Oct. 1, 1987 (Provided in English and in German).

"Grundlagen und Perspektiven der Züchtung von Dreifachnullraps" by S. Pleines, R. Marguard und W. Freidt, Gumpenstein, Osterreich, pp. 115–130 (1987).

1987 and 1988 Tables of Data from Official Canadian Rapeseed CO–OP Trials.

"Biotechnology for Brassica and Helianthus Improvement", Raghav Ram et al., Proceedings of the World Conference on Biotechnology for the Fats and Oils Industry (27th Sep.–2nd Oct. 1987) from American Oil Chemists Society, pp. 65 to 71 (1988).

Proceedings of Sunflower Research Workshop, Feb. 1, 1984, Bismark, North Dakota, pp. 1, 8 and 9.

PRODUCTION OF IMPROVED RAPESEED EXHIBITING AN ENHANCED OLEIC ACID CONTENT

CROSS REFERENCE TO RELATED APPLICATION

This is a Continuation-in-Part of our United States Ser. No. 140,139, filed Dec. 31, 1987 (now abandoned).

BACKGROUND OF THE INVENTION

Rape (i.e., *Brassica napus* and *Brassica campestris*) is being grown as an increasingly important oilseed crop in many parts of the world. As a source of vegetable oil, it presently ranks behind only soybeans and palm and is virtually tied with sunflower for the number three position of commercial importance. The oil is used as both a cooking and salad oil throughout the world.

In its original form rapeseed oil was found to have deleterious effects on human health due to its relatively high level of erucic acid which commonly is present in native cultivars in concentrations of 30 to 50 percent by weight based upon the total fatty acid content. In the past plant scientists identified a germplasm source of low erucic acid rapeseed oil and began incorporating this trait into commercial cultivars. See, Chapter 6 entitled "The Development of Improved Rapeseed Cultivars" by B. R. Stefansson from "High and Low Erucic Acid Rapeseed Oils" edited by John K. G. Kramer, Frank D. Sauer, and Wallace J. Pigden, Academic Press Canada (1983).

In Canada plant scientists focused their efforts on creating so-called "double-low" varieties which were low in erucic acid in the oil and low in glucosinolates in the solid meal remaining after oil extraction (i.e., an erucic acid content of less than 2.0 percent by weight based upon the total fatty acid content, and a glucosinolate content of less than 30 micromoles per gram of the oil-free meal). These higher quality forms of rape developed in Canada are known as canola. In contrast European scientists worked to achieve only "single-low" types which were low in erucic acid, but did not attempt to improve the quality of the solid meal which retained a glucosinolate content of about 100 micromoles per gram of oil-free meal. The result of this major change in the fatty acid composition of rapeseed oil was to create an entirely new oil profile which often contained approximately 62 percent by weight of oleic acid based upon the total fatty acid content. Since the overall percentage of oil in the seed did not change appreciably when the new low erucic cultivars were developed, it appeared that the erucic acid had simply been redirected into other fatty acids with most becoming oleic acid. This level of oleic acid tended to vary within a fairly narrow range of approximately 55 to 65 percent by weight based upon the total fatty acid content. See, Chapter 7 entitled "The Introduction of Low Erucic Acid Rapeseed Varieties Into Canadian Production" by J. K. Daun from the previously identified Academic Press Canada (1983) publication. The weight percent of other fatty acids also varied somewhat, but not enough to define unique types with the potential for distinct uses or added commercial value. See, also "Prospects for the Development of Rapeseed (*B. napus* L.) With Improved Linoleic and Linolenic Acid Content" by N. N. Roy and A. W. Tarr, *Plant Breeding*, Vol. 98, Pages 89 to 96 (1987).

At the present time, canola oil is being marketed by Procter & Gamble under the Puritan trademark. Such vegetable oil typically is free of cholesterol, and the fatty acids present in it consist of approximately 6 percent saturated fatty acids in the form of stearic and palmitic acids, approximately 22 percent by weight linoleic acid which contains two double bonds per molecule of 18 carbon atoms, approximately 10 percent by weight alpha-linolenic acid which contains three double bonds per molecule of 18 carbon atoms, approximately 62 percent by weight oleic acid which contains a single double bond per molecule of 18 carbon atoms, and less than one percent by weight erucic acid which contains a single double bond per molecule of 22 carbon atoms.

Over the years scientists have attempted to improve the fatty acid profile for canola oil. For example, the oxidative stability of the vegetable oil is related to the number of double bonds in its fatty acids. That is molecules with several double bonds are recognized to be more unstable. Thus, scientists have attempted to reduce the content of alpha-linolenic acid in order to improve shelf life and oxidative stability, particularly under heat. This has not proved to be possible through the use of naturally occurring germplasm and the reported values for alpha-linolenic acid for such germplasm have been greater than 6 percent by weight (e.g., greater than 6 up to approximately 12 percent by weight). As reported by Gerhard Röbbelen in Chapter 10 entitled "Changes and Limitations of Breeding for Improved Polyenic Fatty Acids Content in Rapeseed" from "Biotechnology for the Oils and Fats Industry" edited by Colin Ratledge, Peter Dawson, and James Rattray, American Oil Chemists' Society (1984), a mutagenesis experiment was able to achieve lines with less than approximately 3.5 percent by weight of alpha-linolenic acid based upon the total fatty acid content. The profiles of these lines indicate that nearly all of the alpha-linolenic fatty acid was being directed to linoleic acid and that the levels of oleic acid increased only one or two percent. Nevertheless the oil appeared to offer some advantages over normal canola oil. For instance, the refining process required less hydrogenation than normal canola oil and it exhibited a superior fry life.

In recent years studies have established the value of monounsaturated fatty acids as a dietary constituent. This has led to the popularization of the "Mediterranean Diet," with its emphasis on olive oil, a naturally occurring high source of oleic acid. Such a diet is thought to avoid the problem of arteriosclerosis that results from saturated fatty acids. Even in this diet, however, olive oil is thought to be less than ideal, due to its level of saturates. Canola oil is potentially a superior dietary oil, since it contains approximately one-half the saturated fats as olive oil, and since its relatively high levels of alpha-linolenic acid which are deleterious to shelf life and oxidative stability may be a benefit from a dietary point of view. Alpha-linolenic acid is believed to be a precursor for the synthesis by the body of a family of chemicals which may reduce risk from cardiovascular diseases.

It is recognized in the literature that the oleic acid content of canola varies slightly with the environment, temperature, and the moisture availability when the rapeseed is formed. As previously indicated the oleic acid content of available canola cultivars commonly is approximately 55 to 65 percent by weight. See, for instance, Table V at Page 171 from Chapter 7 entitled "The Introduction of Low Erucic Acid Rapeseed Varieties Into Canadian Production" by J. K. Daun appearing in "High and Low Erucic Acid Rapeseed Oils", Academic Press Canada (1983). As reported in the same article, rape varieties which possess greater concentrations of erucic acid will possess even lower oleic acid contents.

Occasionally higher oleic acid contents have been mentioned but have not been made available to the rapeseed grower. For instance, at Page 23 of proceedings of the 7th International Rapeseed Congress held at Poznan, Poland, on May 11 to 14, 1987, passing reference is reported to a canola sample having an oleic content of 79.0 percent under a given set of growing conditions and oleic acid content of 74 percent under different growing conditions. This plant was said to be produced by recurrent selection while employing unidentified parent plants. This is a non-enabling disclosure which will not place the reader of this publication in possession of a rape plant which produces rapeseeds having the increased oleic acid content.

As reported in U.S. Pat. Nos. 4,517,763; 4,658,084; and 4,658,085; and the publications identified therein, hybridization processes suitable for the production of rapeseed are known.

It is an object of the present invention to provide a substantially uniform assemblage of improved rapeseeds which yield a vegetable oil of increased stability.

It is an object of the present invention to provide a substantially uniform assemblage of improved rapeseeds which yield a vegetable oil of increased stability at elevated temperatures which particularly is suited for the deep-frying of food products for human consumption.

It is an object of the present invention to provide a substantially uniform assemblage of improved rapeseeds which yield a vegetable oil which possesses a higher oleic acid content than heretofore available in combination with other desirable traits.

It is an object of the present invention to provide in a preferred embodiment a substantially uniform assemblage of improved rapeseeds which yield a vegetable oil which possesses a higher oleic acid content in combination with a lower alpha-linolenic acid content than heretofore available.

It is another object of the present invention to provide a substantially uniform stand of rape plants capable upon self-pollination of forming rapeseeds which yield a vegetable oil of increased stability.

It is another object of the present invention to provide a substantially uniform stand of rape plants capable upon self-pollination of forming rapeseeds which yield a vegetable oil of increased stability which particularly is suited for the deep-frying of food products for human consumption.

It is another object of the present invention to provide a substantially uniform stand of rape plants capable upon self-pollination of forming rapeseeds which yield a vegetable oil which possesses a higher oleic acid content than heretofore available in combination with other desirable traits.

It is another object of the present invention to provide in a preferred embodiment a substantially uniform stand of rape plants capable upon self-pollination of forming rapeseeds which yield a vegetable oil which possesses a higher oleic acid content in combination with a lower alpha-linolenic acid content than heretofore available.

It is another object of the present invention to provide an improved vegetable oil derived from rapeseeds.

It is a further object of the present invention to provide a method for increasing the oleic acid content of rapeseeds and to thereby improve the stability of the vegetable oil derived therefrom.

These and other objects and advantages of the invention will be apparent to those skilled in the art from a reading of the following description and appended claims.

SUMMARY OF THE INVENTION

A substantially homogeneous assemblage of mature rapeseeds is provided, wherein the rapeseeds are capable of yielding an endogenous vegetable oil of increased stability when exposed to heat, having (1) an oil which exhibits following crushing and extraction an unusually high oleic acid content of at least 80 percent by weight based upon the total fatty acid content, (2) an oil which exhibits following crushing and extraction an erucic acid content of no more than 2.0 percent by weight based on the total fatty acid content, and (3) a glucosinolate content in the solid component following crushing and extraction of the oil of less than 100 micromoles per gram.

A substantially uniform stand of rape plants is provided which upon self-pollination are capable of forming rapeseeds which yield an endogenous vegetable oil of increased stability when exposed to heat, wherein the rapeseeds have (1) an oil which exhibits following crushing and extraction an unusually high oleic acid content of at least 80 percent by weight based upon the total fatty acid content, (2) an oil which exhibits following crushing and extraction an erucic acid content of no more than 2.0 percent by weight based on the total fatty acid content, and (3) a glucosinolate content in the solid component following crushing and extraction of the oil of less than 100 micromoles per gram.

An improved endogenous vegetable oil derived from rapeseeds of increased stability when exposed to heat, said rapeseeds having (1) an oil which exhibits following crushing and extraction an unusually high oleic acid content of at least 79 percent by weight based upon the total fatty acid content, (2) an erucic acid content of no more than 2.0 percent by weight based upon the total fatty acid content, and (3) an oil which exhibits following crushing and extraction an alpha-linolenic acid content less than 5 percent by weight based upon the total fatty acid content.

It has been found that a method of enhancing the oleic acid content of rapeseeds comprises:

(a) subjecting in at least one generation cells derived from a rapeseed plant which forms rapeseeds having an endogenous oleic acid content in the oil of less than 80 percent by weight based on the total fatty acid content to a technique selected from the group consisting of gamma irradiation, contact with a chemical mutagen, and a combination of the foregoing, in order to induce mutagenesis, (b) regenerating said cells to produce a rape plant and to form rapeseed in at least one generation subsequent to that of step (a), (c) selecting a rapeseed produced in step (b) which has an endogenous oleic acid content oil following crushing and extraction of at least 80 percent by weight based upon the total fatty acid content, (d) producing a rape plant on the basis of said selection of step (c), and (e) self-pollinating the rape plant of step (d) for a sufficient number of generations to achieve substantial genetic homogeneity and to form rapeseeds which contain an endogenous oil which exhibits following crushing and extraction an oleic acid content of at least 80 percent by weight based upon the total fatty acid content.

DESCRIPTION OF PREFERRED EMBODIMENTS

Heretofore available rapeseed plants, whether *Brassica napus* or *Brassica campestris*, have formed rapeseeds which possess an oleic acid content of well under 79 percent by weight based upon the total fatty acid content. For the purposes of the present invention the oleic acid content of a given rapeseed is determined by a standard procedure wherein the endogenous oil is removed from the rapeseeds by crushing the seeds and is extracted as a methyl ester following reaction with methanol and sodium hydroxide. Next the resulting ester is analyzed for fatty acid content by gas liquid chromatography using a capillary column which allows separation on the basis of the degree of unsaturation and chain length. This analysis procedure is described in the work of J. K. Daun et al, J. Amer. Oil Chem. Soc. 60:1751–1754 (1983) which is herein incorporated by reference. The higher quality canola varieties of rapeseed which are available for commercial planting commonly possess an oleic acid content of no more than 65 percent by weight based upon the total fatty acid content. Accordingly, a need has persisted in the past for improved canola varieties which exhibit a significantly higher oleic acid content.

In accordance with the concept of the present invention one preferably selects plant cells capable of regeneration (e.g., seeds, microspores, ovules, vegetative parts) from any of the canola varieties which are recognized to have superior agronomic characteristics. Such plant cells may be derived from *Brassica napus* or *Brassica campestris* plants. The *Brassica napus* plants may be of either the summer or winter types. The plant cells derived from a rapeseed plant which forms rapeseeds which possess an oleic acid content of less than 79 percent by weight based upon the total fatty acid content next are subjected in at least one generation to mutagenesis, a rape plant is regenerated from the cells to produce a rape plant and to form rapeseed in at least one subsequent generation, rapeseed is selected having an oleic acid content of at least 79 percent by weight based upon the total fatty acid content, and a rape plant is produced on the basis of this selection which is self-pollinated for a sufficient number of generations (e.g., 2 to 8 additional generations) to achieve substantial genetic homogeneity and to form rapeseeds thereon which contain at least 79 percent oleic acid by weight based upon the total weight of fatty acids present. The plant cells which are subjected to mutagenesis also commonly are from plants which form rapeseeds having an alpha-linolenic content of greater than 5.0 percent by weight (e.g., greater than 3.5 percent by weight), and selection concurrently is made for a reduced alpha-linolenic acid content.

The mutagenesis preferably is carried out by subjecting the plant cells (e.g., a rapeseed) to a technique selected from the group consisting of gamma irradiation, contact with a chemical mutagen, and a combination of the foregoing, for a sufficient duration to accomplish the desired increase in oleic acid content (and preferably also the desired decrease in alpha-linolenic acid content) via a genetic modification but insufficient to destroy the viability of the cells and their ability to be regenerated into a plant. A rapeseed preferably possesses a moisture content of approximately 5 to 6 percent by weight at the time of such mutagenesis. The mutagenesis preferably is carried out by gamma radiation, such as that supplied by a Cesium 137 source. The gamma radiation preferably is supplied to the plant cells (e.g., a rapeseed) in a dosage of approximately 60 to 200 Krad., and most preferably in a dosage of approximately 60 to 90 Krad. It should be understood that even when operating at radiation dosages within the ranges specified, some plant cells (e.g., rapeseeds) will lose their viability and must be discarded. The desired mutagenesis may be accomplished by use of chemical means such as by contact with ethylmethylsulfonate, ethylnitrosourea, etc., and by the use of physical means such as x-ray, etc.

It will be appreciated that the mutagenesis treatment will result in a wide variety of genetic changes within the rape plants which are produced. Many of these changes will be deleterious to the viability of the resulting plant over an extended period of time. Some changes also will produce viable plants which possess deficient agronomic characteristics. Such off-types may be simply discarded. However, if desired plants which have undergone mutation with respect to oleic acid production coupled with undesirable agronomic traits can be retained and used as breeding or source material from which plants having the targeted trait coupled with satisfactory agronomic characteristics are derived.

Following mutagenesis rape plants are regenerated from the treated cells using known techniques. For instance, the resulting rapeseeds may be planted in accordance with conventional rape growing procedures and following self-pollination rapeseed is formed thereon. Alternatively, doubled haploid plantlets may be extracted. The planting of the treated rapeseed preferably is carried out in a greenhouse in which the pollination is carefully controlled and monitored. Additional rapeseed which is formed as a result of such self-pollination in the present or a subsequent generation is harvested and is subjected to analysis for oleic acid content. Since *Brassica napus* and *Brassica campestris* are dicotyledons, the analysis for oleic acid can be carried out on a halfseed, and the remaining halfseed can be retained for possible future germination if the oleic acid content is found to be favorable as a result of the mutagenesis. The rapeseeds can be carefully separated into two halfseeds using known techniques.

When a mature halfseed is found to possess an oleic content of at least 79 percent by weight (preferably at least 80 percent by weight), it is selected and retained. The oleic acid content of such selection preferably will be 79 to 90 percent by weight (e.g., 80 to 85 percent by weight).

The other halfseed (i.e., cotyledon) which will be genetically the same as the halfseed which was subjected to halfseed analysis can next be caused to germinate and a rape plant is formed and allowed to undergo self-pollination. Such planting of the halfseed preferably also is carried out in a greenhouse in which the pollination is carefully controlled and monitored. The resulting rapeseed is harvested, planted, and is self-pollinated for a sufficient number of generations to achieve substantial genetic homogeneity. The genetic stabilization of the rape plant material enables the creation of plants having a reasonably predictable genotype which can be used as breeding or source material for the production of other improved rape varieties, as a finished variety for use by the rapeseed grower, or as a parent in the production of hybrid rapeseed with the high oleic acid content being transferred to the progeny.

The resulting rapeseeds also are selected so that they possess the erucic acid and glucosinolate contents of canola. More specifically, the erucic acid content is no more than 2.0 percent by weight based upon the total fatty acid content, and preferably less than 0.1 percent by weight (e.g., less than 0.05 percent by weight) based on the total fatty acid content, and the glucosinolate content in the solid component is less than 100 micromoles per gram (preferably less than 30 micromoles per gram). The glucosinolate content may be any one or a mixture of 3-butenyl glucosinolate, 4-pentenyl glucosinolate, 2-hydroxy-3-butenyl glucosinolate, and 2-hydroxy-4-pentenyl gluconsinolate. The gluconsinolate determination preferably is made on the air-dry-oil-free solid as measured by the gas liquid chromatograph method of the Canadian Grain Commission. The erucic acid and glucosinolate levels commonly are made possible by selecting starting materials which already possess highly desirable levels of these components. In a preferred embodiment wherein the vegetable oil is intended for frying applications the resulting rapeseeds also are selected which have an alpha-linolenic acid content less than 5 percent by weight based upon the total fatty acid content (e.g., preferably no more than 3.5 percent by weight based upon the total fatty acid content). Also, in a preferred embodiment the vegetable oil contains no more than 7 percent by weight of saturated fatty acids in the form of stearic and palmitic acids based upon the total fatty acid content (e.g., 6 to 7 percent by weight).

The desired traits described herein (e.g., unusually high oleic acid content) once established can be readily transferred into other plants within the same Brassica napus or Brassica campestris species by conventional plant breeding techniques involving cross-pollination and selection of the progeny. It has been demonstrated that the characteristics are highly heritable, can be transmitted to their progeny, and can be recovered in segregating progeny in subsequent generations following crossing. Also, once established the desired traits can be transferred between the napus and campestris species using the same conventional plant breeding techniques involving pollen transfer and selection. The transfer of other traits, such as low erucic acid content, between the napus and campestris species by standard plant breeding techniques is already well documented in the technical literature. See, for instance, Brassica Crops and Wild Allies Biology and Breeding, edited by S. Tsunada, K. Hinata, and Gomez Campo, Japan Scientific Press, Tokyo (1980). As an example of the transfer of the desired traits described herein (e.g., unusually high oleic acid content) from napus to campestris, one may select a commercially available campestris variety such as Tobin, Horizon, or Colt and carry out an interspecific cross with an appropriate plant of the napus breeding lines discussed hereafter (e.g., FA677-39, Topas H6-90 and FA677M5-132). Alternatively, other napus breeding lines may be reliably and independently developed when following the mutagenesis techniques described herein. The Tobin variety is available from Agriculture Canada, Saskatoon, Saskatchewan, and other distributors. The Horizon and Colt varieties are available from Bonis & Company Ltd. of Lindsay, Ontario, Canada. Following the interspecific cross, members of the $F_1$ generation are self-pollinated to produce $F_2$ seed. Selection for the desired traits (e.g., unusually high oleic acid content) is then conducted on single $F_2$ seeds which are then backcrossed with the campestris parent through the number of generations required to obtain a euploid (n=10) campestris line exhibiting the desired traits (e.g., unusually high oleic acid content).

In accordance with the concept of the present invention the rapeseeds possessing the specified combination of characteristics are multiplied to form a substantially uniform assemblage of such seeds (e.g., a bag of such seeds) which can be used to produce a substantially uniform stand of such rape plants. The rapeseeds present in such assemblage number at least 250 seeds, and the resulting substantially uniform stand of rape plants numbers at least 250 plants.

The improved vegetable oil of the present invention may be formed by simple extraction in a direct manner from the mature rapeseeds such as by crushing and extraction in accordance with known techniques. See, for example, Chapter 8 entitled "Rapeseed Crushing and Extraction" by D.H.C. Beach appearing in "High and Low Erucic Acid Rapeseed Oils," Academic Press Canada (1983) which is herein incorporated by reference. In a preferred embodiment the vegetable oil is present in a quantity convenient for commercial or domestic use (e.g., a quantity of at least one liter).

The theory whereby the mutagenesis has been found to be capable of increasing the oleic acid content to such high levels in rape is considered to be complex and incapable of simple explanation. For instance, the mutation may adversely impact upon the formation of one or more enzymes which normally would function in dehydrogenation of the fatty acids as the seeds mature.

The following Examples are presented as a specific illustrations of the claimed invention. It should be understood, however, that the invention is not limited to the specific details set forth in the Examples.

EXAMPLE I

Seeds of the Regent variety of Brassica napus were selected as the starting material. This variety of canola is of the summer type and is suitable to produce vegetable oil when grown in the north central region of the United States, the western prairie area of Canada, and other areas where summer rape is adapted. The Regent variety was first introduced in 1977 by the University of Manitoba. Planting seed for the Regent variety is available from the Department of Plant Science of the University of Manitoba. A representative sample (i.e., 2.0 grams) of the mature seeds of the starting material prior to subjection to gamma radiation (as described hereafter) contained the following fatty acids in the approximate concentrations indicated based upon the total weight of the fatty acids present while using gas liquid chromatography analysis technique previously described:

| Fatty Acid | Number of Carbon Atoms Per Molecule | Number of Double Bonds Per Molecule | Weight Percent |
| --- | --- | --- | --- |
| Palmitic | 16 | 0 | 4.8 |
| Palmitoleic | 16 | 1 | 0.1 |
| Stearic | 18 | 0 | 1.6 |
| Oleic | 18 | 1 | 65.4 |
| Linoleic | 18 | 2 | 19.3 |
| Alpha-Linolenic | 18 | 3 | 6.9 |
| Arachidic | 20 | 0 | 0.6 |
| Eicosenoic | 20 | 1 | 1.0 |
| Behenic | 22 | 0 | 0.3 |
| Erucic | 22 | 1 | non-detectable |

The gluconsinolate content in the solid component was 13.44 micromoles per gram as determined by the gas liquid chromatograph method of the Canadian Grain Commission.

Prior to gamma irradiation the seeds of the Regent variety of canola were stored under conditions so as to maintain viability. More specifically, the seeds were stored in a cold storage room maintained at approximately 10° C. and 40 percent relative humidity, and contained a moisture content of approximately 5.5 percent by weight following air drying.

Seeds of the Regent variety (i.e., approximately 10 grams) next were placed in a Gammacell 1000 gamma irradiation apparatus manufactured by Atomic Energy of Canada, Ltd. where they were subjected 90 Krad. of irradiation produced by a Cesium 137 source at a rate of 26.61 Krad. per hour in order induce mutagenesis. These seeds can be termed M1 seeds.

The M1 seeds following subjection to gamma irradiation were planted in a greenhouse at Georgetown, Ontario, Canada, having a day temperature of approximately 25°±3° C., and a night temperature of approximately 18° C. Approximately 40 percent of the gamma irradiated seeds produced fertile rape plants which upon self-pollination yielded M2 seeds. The M2 seeds were next planted in the field at the same location to produce plants which following pollination produced M3 seeds.

Representative M3 seeds produced on the M2 plants next were soaked in water and one cotyledon from each seed was carefully removed for the analysis of its fatty acid composition using the gas liquid chromatography analysis technique previously described. Such halfseed analysis was carried out in accordance with the procedure of "Methods for Breeding for Oil Quality in Rape" by R. K. Downey and B. L. Harvey reported in *Canadian Journal of Plant Science*, Vol. 43, Pages 271 to 275 (1963) which is herein incorporated by reference. From a total of 4490 cotyledon analyses from M3 plants, 37 cotyledons were determined to contain an increased oleic acid content within the range of 70.2 to 76 percent based upon the total fatty acid content, and an alpha-linolenic acid content within the range of 5.4 to 13.1 percent based upon the total fatty acid content.

An M3 halfseed designated as FA 677 was selected which was found to contain the following fatty acids in the concentrations indicated based upon the total weight of fatty acids present:

| Fatty Acid | Number of Carbon Atoms Per Molecule | Number of Double Bonds Per Molecule | Weight Percent |
| --- | --- | --- | --- |
| Palmitic | 16 | 0 | 4.0 |
| Palmitoleic | 16 | 1 | non-detectable |
| Stearic | 18 | 0 | 1.4 |
| Oleic | 18 | 1 | 70.9 |
| Linoleic | 18 | 2 | 10.7 |
| Alpha-Linolenic | 18 | 3 | 11.0 |
| Arachidic | 20 | 0 | 0.5 |
| Eiscosenoic | 20 | 1 | 1.2 |
| Behenic | 22 | 0 | 0.3 |
| Erucic | 22 | 1 | non-detectable |

All the M3 halfseeds including FA 677 were planted in the greenhouse and were caused to undergo self-pollination and to form the M4 generation. Each of these plants produced sufficient seed for random 50 seed samples from each plant to be crushed and analyzed by gas liquid chromatography. When these representative 50 seed samples from the M4 generation were analyzed, it was found that the oleic acid content ranged from 63 to 80 percent by weight based upon the total fatty acid content, and the alpha-linolenic acid content ranged from 3.2 to 7.7 percent by weight based upon the total fatty acid content. The single plant designated FA 677 was found to have the highest oleic acid content (i.e., 80 percent). Sixty-five seeds from this plant were planted to grow the M5 generation. For reference purposes, 50 of these 65 seeds were also subjected to cotyledon analysis, which revealed oleic acid levels ranging from 74.0 to 85.0 percent by weight based upon the total fatty acid content. The cotyledon analysis-derived profile of the best plant (85.0 percent oleic acid) is shown in the table below:

| Fatty Acid | Number of Carbon Atoms Per Molecule | Number of Double Bonds Per Molecule | Weight Percent |
| --- | --- | --- | --- |
| Palmitic | 16 | 0 | 3.2 |
| Palmitoleic | 16 | 1 | 0.2 |
| Stearic | 18 | 0 | 2.4 |
| Oleic | 18 | 1 | 85.0 |
| Linoleic | 18 | 2 | 4.4 |
| Alpha-Linolenic | 18 | 3 | 2.7 |

-continued

| Fatty Acid | Number of Carbon Atoms Per Molecule | Number of Double Bonds Per Molecule | Weight Percent |
| --- | --- | --- | --- |
| Arachidic | 20 | 0 | 1.0 |
| Eicosenoic | 20 | 1 | 1.2 |
| Behenic | 22 | 0 | non-detectable |
| Erucic | 22 | 1 | non-detectable |

The specific FA 677 plant identified above which produced the oleic acid content of 85 percent by weight based upon the total fatty acid content was lost in the next generation through raceme breakage in the greenhouse. However, when a 50 seed sample from a sister plant in the M5 generation, designated FA 677-39, was analyzed after crushing, the following fatty acids were observed in the concentrations indicated based upon the total weight of the fatty acids present. The plants resulting from the germination of the seeds exhibited a substantially uniform phenotype.

| Fatty Acid | Number of Carbon Atoms Per Molecule | Number of Double Bonds Per Molecule | Weight Percent |
| --- | --- | --- | --- |
| Myristic | 14 | 0 | 0.1 |
| Palmitic | 16 | 0 | 4.1 |
| Palmitoleic | 16 | 1 | 0.3 |
| Stearic | 18 | 0 | 1.6 |
| Oleic | 18 | 1 | 79.2 |
| Linoleic | 18 | 2 | 7.1 |
| Alpha-Linolenic | 18 | 3 | 4.6 |
| Arachidic | 20 | 0 | 0.7 |
| Eicosenoic | 20 | 1 | 1.5 |
| Behenic | 22 | 0 | 0.5 |
| Erucic | 22 | 1 | 0.06 |
| Lignoceric | 24 | 0 | 0.3 |

The gluconsinolate content in the solid component was 10.94 micromoles per gram. The plants produced from the seed are true-breeding upon self-pollination and exhibit a substantially uniform phenotype. Significantly, the average oleic acid content of all of the samples analyzed (65 samples, 50 seeds per sample) was 77.1 percent by weight based upon the total fatty acid content indicating a stably high oleic acid level in all descendents of the plant designated FA 677.

Further selections using the FA677-39 breeding line can result in the identification of plants exhibiting even higher oleic acid contents. These plants can be preserved and multiplied using conventional techniques.

The increased oleic acid content renders the rapeseeds capable of providing a vegetable oil of increased stability when exposed to heat. Accordingly, the resulting oil can reliably be used for food-frying applications for a more extended period of time without deleterious results when compared to the canola oil of the prior art. Also, the reduced alpha-linolenic acid content of the resulting vegetable oil imparts enhanced oxidative stability to the same.

Comparable rapeseed seeds of the M5 generation designated FA 677-39 have been deposited under the Budapest Treaty in the American Type Culture Collection, 12301 Parklawn Drive, Rockville, Md. 20852, U.S.A., on Dec. 31, 1987. This seed deposit has received Accession No. 40409, and will be made available upon the maturation of this application into a patent. However, the availability of these seeds is not to be construed as a license to practice this invention in contravention of the rights granted under the authority of any government in accordance with its patent or breeder's rights laws.

EXAMPLE II

Twelve selections from the M5 generation (discussed with respect to Example I) having the highest oleic acid contents were subjected to further mutagenesis while employing a chemical mutagen. More specifically, two composite seed lots of these selections were formed consisting of 1,000 seeds each and were treated with ethylnitrosourea. The ethylnitrosourea was present in a dimethylsulfoxide solvent at a concentration of 8 mM. (millimoles). During the preparation of the ethylnitrosourea solution 25 ml. of dimethylsulfoxide were added to one gram of ethylnitrosourea and the resulting solution was buffered at a pH of 5.5 with 5 mM. (millimoles) of morpholinoethanesufonic acid. Each seed lot was placed in a large petri dish and 30 ml. of the resulting solution were added. The seeds while in contact with the ethylnitrosourea solution were incubated in the dark at 20° C. for 18 hours, were rinsed three times with distilled water, and were planted in flats present in a greenhouse containing a soilless greenhouse growing media. 500 seeds were planted per flat.

Approximately 30 percent of the seeds which were treated with the ethylnitrosourea solution grew into plants, the plants were transplanted into pots, the potted plants were grown in a greenhouse, and approximately 25 percent of these exhibited sufficient fertility to undergo self-pollination and to produce seed (i.e., the M2 generation following mutagenesis while employing a chemical mutagen).

Seeds (i.e., the M2 generation) were next harvested from 153 plants (i.e., the M1 plants). Ten seeds from each of the plants were individually analyzed by the halfseed analysis previously described. A total of 276 cotyledon selections were obtained having an oleic acid level of 77 percent by weight or higher based upon the total fatty acid content. Three of these selections were found to contain an oleic acid content of 84 percent by weight based upon the total fatty acid content.

The remaining cotyledons from the 276 selections were planted in a greenhouse at Georgetown, Ontario, Canada having a day temperature of approximately 25°±3° C. and a night temperature of approximately 18° C., plants were formed, and seeds were formed as the result of self-pollination (i.e., the M3 generation following mutagenesis while employing a chemical mutagen). A selection designated FA677M5-132 in the M3 generation was found to exhibit while using two random 50 seed bulk analyses an oleic acid content of 81.9 percent by weight based upon the total fatty acid content, an alpha-linolenic acid content of 4.03 percent by weight based upon the total acid content, a non-detectible erucic acid content, a saturated fatty acid content of 6.59 percent by weight in the form of stearic and palmitic acids based upon the total fatty acid content, and a glucosinolate content in the solid component of less than 30 micromoles per gram. The plants resulting from the germination of the seeds exhibited a substantially uniform phenotype. Further selections from within the FA677M5-132 breeding line will result in the identification of plants exhibiting even higher oleic acid contents. These plants can be preserved and multiplied using conventional techniques. For instance, when analyzing single cotyledons of this breeding line, oleic acid contents higher than 85 percent by weight based upon the total fatty acid content have been observed.

Comparable rapeseeds of the M3 generation designated FA677M5-132 have been deposited under the Budapest Treaty in the American Type Culture Collection, 12301 Parklawn Drive, Rockville, Md. 20852, U.S.A., on Dec. 13, 1988. This seed deposit has received Accession No. 40523, and will be made available upon the maturation of this application into a patent. However, the availability of these seeds is not to be construed as a license to practice this invention in contravention of the rights granted under the authority of any government in accordance with its patent or breeder's rights laws.

EXAMPLE III

Seeds of Topas variety of *Brassica napus* were selected as the starting material. This variety of canola is of the summer type and is suitable to produce vegetable oil when grown in the United States, Canada, Sweden, and other areas where summer rape is adapted. The Topas variety was registered in 1987 by Svaldof AB of Sweden. Planting seed for this variety is available from Bonis & Company Ltd. of Lindsay, Ontario, Canada. This variety typically exhibits an oleic acid content of approximately 65 percent by weight based upon the total fatty acid content and an alpha-linolenic acid content of approximately 8 percent by weight based upon the total fatty acid content.

Ten thousand seeds of the Topas variety were subjected to mutagenesis while employing a chemical mutagen. More specifically, seed lots were formed consisting of 1,000 seeds each and were treated with ethylnitrosourea as previously described. The resulting seeds were planted in flats present in a greenhouse containing a soilless greenhouse growing media. 500 seeds were planted in each flat and can be termed M1 seeds.

Seeds (i.e., the M2 generation) were formed as the result of self-pollination on 111 surviving fertile plants (i.e., the M1 plants). One of the M2 seeds when subjected to cotyledon analysis exhibited on oleic acid content of 82.07 percent by weight and an alpha-linolenic acid content of 5.12 percent by weight based upon the total fatty acid content. The remaining M2 cotyledon was planted in a greenhouse at Georgetown, Ontario, Canada, having a day temperature of approximately 25°±3° C. and a night temperature of approximately 18° C., a plant was formed, and seeds were formed as the result of self-pollination (i.e., the M3 generation). This M3 generation was designated Topas H6-90 and was found to exhibit while using two random 50 seed bulk analyses an oleic acid content of 81.17 percent by weight based upon the total fatty acid content, an alpha-linolenic acid content of 3.55 percent by weight based upon the total fatty acid content, a non-detectible erucic acid content, a saturated fatty acid content of 6.17 percent by weight in the form of stearic and palmitic acids based upon the total fatty acid content, and a glucosinolate content in the solid component of less than 30 micromoles per gram. The plants resulting from the germination of the seeds exhibited a substantially uniform phenotype. Further selections from within the Topas H6-90 breeding line (as indicated hereafter) will result in the identification of plants exhibiting even higher oleic acid contents. These plants can be preserved and multiplied using conventional techniques.

Comparable rapeseeds of the M3 generation designated Topas H6-90 have been deposited under the Budapest Treaty in the American Type Culture Collection, 12301 Parklawn Drive, Rockville, Md. 20852, U.S.A., on Dec. 13, 1988. This seed deposit has received Accession No. 40524, and will be made available upon the maturation of this application into a patent. However, the availability of these seeds is not to be construed as a license to practice this invention in contravention of the rights granted under the authority of any government in accordance with its patent or breeder's rights law.

Further selection within the M3 generation of Topas H6-90 identified a selection identified as Topas H6-90-99 containing the following fatty acids in the approximate concentrations indicated based upon the total fatty acids present while using the same gas liquid chromatography analysis technique previously described:

| Fatty Acid | Number of Carbon Atoms Per Molecule | Number of Double Bonds Per Molecule | Weight Percent |
|---|---|---|---|
| Palmitic | 16 | 0 | 3.57 |
| Palmitoleic | 16 | 1 | 0.31 |
| Stearic | 18 | 0 | 1.87 |
| Oleic | 18 | 1 | 85.84 |
| Linoleic | 18 | 2 | 3.54 |
| Alpha-Linolenic | 18 | 3 | 2.68 |
| Arachidic | 20 | 0 | 0.49 |
| Eicosenoic | 20 | 1 | 1.29 |
| Behenic | 22 | 0 | 0.32 |
| Erucic | 22 | 1 | non-detectable |
| Lignoceric | 24 | 0 | 0.07 |

Seeds produced from H6-90-99 will continue to exhibit a glucosinolate content in the solid component of less than 30 micromoles per gram.

Although the invention has been described with preferred embodiments, it is to be understood that variations and modifications may be resorted to as will be apparent to those skilled in the art. Such variations and modifications are to be considered within the purview and scope of the claims appended hereto.

We claim:

1. A substantially homogeneous assemblage of mature rapeseeds, capable of yielding an endogenous vegetable oil of increased stability when exposed to heat, having (1) an oil which exhibits following crushing and extraction an unusually high oleic acid content of 80 to 90 percent by weight based upon the total fatty acid content wherein said oleic acid content is controlled by genetic means for the expression of such trait resulting from a mutation induced by man followed by selection, and (2) an oil which exhibits following crushing and extraction a erucic acid content of no more than 2.0 percent by weight based on the total fatty acid content.

2. A substantially homogeneous assemblage of seeds according to claim 1 wherein said rapeseeds were formed on *Brassica napus* plants.

3. A substantially homogeneous assemblage of seeds according to claim 1 wherein said rapeseeds were formed on *Brassica campestris* plants.

4. A substantially homogeneous assemblage of seeds according to claim 1 wherein said rapeseeds were formed on plants which exhibit a substantially uniform phenotype.

5. A substantially homogeneous assemblage of rapeseeds according to claim 1 which have an endogenous oil which exhibits following crushing and extraction an unusually high oleic acid content of 80 to 85 percent by weight based upon the total fatty acid content.

6. A substantially homogeneous assemblage of rapeseeds according to claim 1 which have an endogenous oil which exhibits following crushing and extraction a erucic acid content of less than 0.1 percent by weight based on the total fatty acid content.

7. A substantially homogeneous assemblage of rapeseeds according to claim 1 which have an endogenous oil which exhibits following crushing and extraction a erucic acid content of less than 0.05 percent by weight based upon the total fatty acid content.

8. A substantially homogeneous assemblage of rapeseeds according to claim 1 which additionally have an endogenous oil which exhibits following crushing and extraction an alpha-linolenic acid content of less than 5 percent by weight based upon the total fatty acid content.

9. A substantially homogeneous assemblage of rapeseeds according to claim 1 which additionally have an endogenous oil which exhibits following crushing and extraction an alpha-linolenic acid content of no more than 3.5 percent by weight based upon the total fatty acid content.

10. A substantially homogeneous assemblage of rapeseeds according to claim 1 wherein said unusually high oleic acid content is the result of a mutation induced by man with the use of a technique selected from the group consisting of gamma irradiation, contact with a chemical mutagen, and a combination of the foregoing, in at least one earlier generation followed by selection.

11. A substantially homogeneous assemblage of rapeseeds according to claim 1 wherein said rapeseeds upon growing and self-pollination are true-breeding for said oleic acid, and erucic acid, contents.

12. A substantially homogeneous assemblage of rapeseeds according to claim 1 which comprises at least 250 seeds.

13. A substantially homogenous assemblage of rapeseeds according to claim 1 wherein said genetic means for the expression of said unusually high oleic acid content is derived from through at least one step selected from the group consisting of selection from, cross breeding with, and mutation of FA 677-39.

14. A substantially homogeneous assemblage of rapeseeds according to claim 1 wherein said genetic means for the expression of said unusually high oleic acid content is derived from FA677M5-132.

15. A substantially homogeneous assemblage of rapeseeds according to claim 1 wherein said genetic means for the expression of said unusually high oleic acid content is derived from Topas H6-90.

16. A substantially homogeneous assemblage of rapeseeds according to claim 1 which additionally have a gluconsinolate content in the solid component following crushing and extraction of the oil of less than 100 micromoles per gram.

17. A substantially homogeneous assemblage of rapeseeds according to claim 16 which have a glucosinolate content in the solid component following crushing and extraction of the oil of less than 30 micromoles per gram.

18. A substantially homogeneous assemblage of seeds according to claim 1 which were produced in the field under conventional rape growing conditions.

19. A substantially uniform stand of rape plants which upon self-pollination are capable of forming rapeseeds which yield an endogenous vegetable oil of increased stability when exposed to heat, said rapeseeds having (1) an oil which exhibits following crushing and extraction an unusually high oleic acid content of 80 to 90 percent by weight based upon the total fatty acid content wherein said oleic acid content is controlled by genetic means for the expression of such trait resulting from a mutation induced by man followed by selection, and (2) an oil which exhibits following crushing and extraction a erucic acid content of no more than 2.0 percent by weight based on the total fatty acid content.

20. A substantially uniform stand of rape plants according to claim 19 wherein said plants are *Brassica napus*.

21. A substantially uniform stand of rape plants according to claim 19 wherein said plants are *Brassica campestris*.

22. A substantially uniform stand of rape plants according to claim 19 wherein said plants exhibit a substantially uniform phenotype.

23. A substantially uniform stand or rape plants according to claim 19 wherein said rapeseeds have an endogenous oil which exhibits following crushing and extraction an unusually high oleic acid content of 80 to 85 percent by weight based upon the total fatty acid content.

24. A substantially uniform stand of rape plants according to claim 19 wherein said rapeseeds have oil which exhibits following crushing and extraction a erucic acid content of less than 0.1 percent by weight based upon the total fatty acid content.

25. A substantially uniform stand of rape plants according to claim 19 wherein said rapeseeds have an endogenous oil which exhibits following crushing and extraction a erucic acid content of 0.05 percent by weight based upon the total fatty acid content.

26. A substantially uniform stand of rape plants according to claim 19 wherein said rapeseeds additionally have an endogenous oil which exhibits following crushing and extraction an alpha-linolenic acid content of less than 5 percent by weight based upon the total fatty acid content.

27. A substantially uniform stand of rape plants according to claim 19 wherein said rapeseeds additionally have an endogenous oil which exhibits following crushing and extraction an alpha-linolenic acid content of no more than 3.5 percent by weight based upon the total fatty acid content.

28. A substantially uniform stand of rape plants according to claim 19 wherein said unusually high oleic acid content of said rapeseeds is the result of a mutation which was induced by man with the use of a technique selected from the group consisting of gamma irradiation, contact with a chemical mutagen, and a combination of the foregoing, in at least one earlier generation followed by selection.

29. A substantially uniform stand of rape plants according to claim 19 which comprises at least 250 plants.

30. A substantially uniform stand of rape plants according to claim 19 wherein said genetic means for the expression of said unusually high oleic acid content is derived from through at least one step selected from the group consisting of selection from, cross breeding with, and mutation of FA 677-39.

31. A substantially uniform stand of rape plants according to claim 19 wherein said genetic means for the expression of said unusually high oleic acid content is derived from FA677M5-132.

32. A substantially uniform stand of rape plants according to claim 19 wherein said genetic means for the expression of said unusually high oleic acid content is derived from Topas H6-90.

33. A substantially uniform stand of rape plants according to claim 19 wherein said rapeseeds have a gluconsinolate content in the solid component of less than 100 micromoles per gram.

34. A substantially uniform stand of rape plants according to claim 33 wherein said rapeseeds have a glucosinolate content in the solid component following crushing and extraction of the oil of less than 30 micromoles per gram.

35. A substantially uniform stand of rape plants according to claim 19 which were produced in the field under conventional rape growing conditions.

36. A method for enhancing the oleic acid content of rapeseeds comprising:

(a) subjecting in at least one generation cells derived from a rapeseed plant which forms rapeseeds having an endogenous oleic acid content in the oil of less than 80 percent by weight based on the total fatty acid content to a technique selected from the group consisting of gamma in addition, contact with a chemical mutagen, and a combination of the foregoing, in order to induce mutagenesis with respect to the increased production of oleic acid, (b) regenerating said cells to produce a rape plant and to form rapeseeds in at least one generation subsequent to that of step (a), (c) selecting a rapeseed produced in step (b) which has an endogenous oleic acid content in the oil following crushing and extraction of at least 80 percent by weight based upon the total fatty acid content, and (d) producing rape plants in a subsequent generation derived from said selection of step (c) having substantial genetic homogeneity and forming rapeseeds thereon which contain an endogenous oil which exhibits following crushing and extraction an oleic acid content of 80 to 90 percent by weight based upon the total fatty acid content wherein said oleic acid content is controlled by genetic means for the expression of such trait resulting from such mutagenesis.

37. A method for enhancing the oleic acid content of rapeseeds according to claim 36 wherein said cells derived from a rapeseed plant in step (a) are present in the form of a rapeseed seed.

38. A method for enhancing the oleic acid content of rapeseeds according to claim 36 wherein during step (a) said cells are present in the form of a rapeseed seed having a moisture content of approximately 5 to 6 percent by weight and are subjected to approximately 60 to 200 Krad. of gamma irradiation.

39. A method for enhancing the oleic acid content of rapeseeds according to claim 36 wherein during step (a) said cells are present in the form of a rapeseed seed having a moisture content of approximately 5 to 6 percent by weight and are subjected to approximately 60 to 90 Krad. of gamma irradiation.

40. A method for enhancing the oleic acid content of rapeseeds according to claim 36 wherein said mutagenesis is carried out at least in part by contact with a chemical mutagen.

41. A method for enhancing the oleic acid content of rapeseeds according to claim 40 wherein said chemical mutagen is ethylnitrosourea.

42. A method for enhancing the oleic acid content of rapeseeds according to claim 36 wherein said product of step (e) additionally has an endogenous erucic acid content of no more than 2.0 percent by weight following crushing and extraction based on the total fatty acid content and a glucosinolate content in the solid component following crushing and extraction of the oil of less than 100 micromoles per gram.

43. A method for enhancing the oleic acid content of rapeseeds according to claim 36 wherein said product of step (e) additionally has an endogenous erucic acid content of less than 0.1 percent by weight following crushing and extraction based on the total fatty acid content and a glucosinolate content in the solid component following crushing and extraction of the oil of less than 30 micromoles per gram.

44. A method for enhancing the oleic acid content of rapeseeds according to claim 36 wherein said starting material of step (a) is present in the form of a rapeseed seed which additionally has an endogenous alpha-linolenic acid content in the oil greater than 5 percent by weight following crushing and extraction based upon the total fatty acid content, said step (c) includes a selection which additionally has in the oil an alpha-linolenic acid content following crushing and extraction of less than 5 percent by weight, and the product of step (e) additionally has in the oil an alpha-linolenic acid content following crushing and extraction of less than 5 percent by weight.

45. A method of enhancing the oleic acid content of rapeseeds according to claim 36 wherein said starting material of step (a) is present in the form of a rapeseed seed which additionally has an endogenous alpha-linolenic acid content in the oil greater than 3.5 percent by weight following crushing and extraction based upon the total fatty acid content, said step (c) includes a selection which additionally has in the oil an alpha-linolenic acid content of no more than 3.5 percent by weight following crushing and extraction, and the product of step (e) additionally has in the oil an alpha-linolenic acid content of no more than 3.5 percent by weight following crushing and extraction.

46. A method for enhancing the oleic acid content of rapeseeds according to claim 36 wherein said rape plants of step (d) are the result of self-pollination for a sufficient number of generations to achieve substantial genetic homogeneity.

47. A method for enhancing the oleic acid content of rapeseeds according to claim 36 wherein in step (d) said rape plants are produced in the field under conventional rape growing conditions.

48. An improved endogenous vegetable oil of increased stability when exposed to heat extracted from rapeseeds formed on said rape plants of step (d) of claim 36, said rapeseeds having (1) an oil which exhibits following crushing and extraction an unusually high oleic acid content of 80 to 90 percent by weight based upon the total fatty acid content, (2) an oil which exhibits following crushing and extraction a erucic acid content of no more than 2.0 percent by weight based on the total fatty acid content, and (3) an oil which exhibits following crushing and extraction an alpha-linolenic acid content of less than 5 percent by weight based upon the total fatty acid content.

49. An improved vegetable oil extracted from rapeseeds according to claim 48 wherein said rapeseeds were formed on *Brassica napus* plants.

50. An improved vegetable oil extracted from rapeseeds according to claim 48 wherein said rapeseeds were formed on *Brassica campestris* plants.

51. An improved vegetable oil extracted from rapeseeds according to claim 48 wherein said rapeseeds have an endogenous oil which exhibits following crushing and extraction an unusually high oleic acid content of 80 to 85 percent by weight based upon the total fatty acid content.

52. An improved vegetable oil extracted from rapeseeds according to claim 48 wherein said rapeseeds have an endogenous oil which exhibits following crushing and extraction a erucic acid content of less than 0.1 percent by weight based upon the total fatty acid content.

53. An improved vegetable oil extracted from rapeseeds according to claim 48 wherein said rapeseeds have an endogenous oil which exhibits following crushing and extraction a erucic acid content of less than 0.05 percent by weight based upon the total fatty acid content.

54. An improved vegetable oil extracted from rapeseeds according to claim 48 wherein said rapeseeds have an endogenous oil which exhibits following crushing an extraction an alpha-linolenic acid content of no more than 3.5 percent by weight based upon the total fatty acid content.

55. An improved vegetable oil extracted from rapeseeds according to claim 48 wherein said unusually high oleic acid content is the result of a mutation induced by man with the use of a technique selected from the group consisting of gamma irradiation, contact with a chemical mutagen, and a combination of the foregoing, in at least one earlier generation followed by selection.

56. An improved vegetable oil extracted from rapeseeds according to claim 48 which is present in a quantity of at least one liter.

57. An improved endogenous vegetable oil extracted from rapeseeds according to claim 48 wherein said genetic means for the expression of said unusually high oleic acid content is derived from through at least one step selected from the group consisting of selection from, cross breeding with, and mutation of FA 677-39.

58. An improved endogenous vegetable oil extracted from rapeseeds according to claim 48 wherein said genetic means for the expression of said unusually high oleic acid content is derived from FA677M5-132.

59. An improved endogenous vegetable oil extracted from rapeseeds according to claim 48 wherein said genetic means for the expression of said unusually high oleic acid content is derived from Topas H6-90.

* * * * *